United States Patent [19]

Mancini et al.

[11] 4,317,780

[45] Mar. 2, 1982

[54] ORGANIC ESTER FOR USE IN LUBRICANT COMPOSITIONS

[75] Inventors: Giuseppe Mancini, Melegnano; Luigi Imparato, Milan; Franco Berti, San Donato Milanese, all of Italy

[73] Assignee: Snamprogetti S.p.A., Milan, Italy

[21] Appl. No.: 110,189

[22] Filed: Jan. 7, 1980

Related U.S. Application Data

[63] Continuation of Ser. No. 971,814, Dec. 21, 1978, abandoned, which is a continuation of Ser. No. 908,357, May 22, 1978, abandoned, which is a continuation of Ser. No. 731,992, Oct. 13, 1976, abandoned.

[30] Foreign Application Priority Data

Dec. 11, 1975 [IT] Italy .............................. 30195 A/75

[51] Int. Cl.$^3$ .......................... C09F 5/08; C11C 3/00
[52] U.S. Cl. .............................. 260/410.6; 252/56 S; 560/263
[58] Field of Search ................... 260/410.6; 252/56 S; 560/263

[56] References Cited

U.S. PATENT DOCUMENTS

| | | | |
|---|---|---|---|
| 3,670,013 | 6/1972 | Leibfried | 260/410.6 X |
| 3,694,382 | 9/1972 | Kleiman | 252/56 S |
| 4,025,447 | 5/1977 | Mancini et al. | 260/410.6 X |

*Primary Examiner*—John F. Niebling
*Attorney, Agent, or Firm*—Morgan, Finnegan, Pine, Foley & Lee

[57] ABSTRACT

Organic esters, to be employed to make up lubricating compositions are disclosed, said esters being the products of the reaction between a diol and a triol, on the one hand, and a mixture of saturated monocarboxylic acids, on the other hand. The ratios of the diol to the triol (molarly) and the structure and number of carbon atoms of the saturated monocarboxylic acids are critical. Critical values are given, as well as examples of practical use; the viscosity and viscosity index properties of the novel esters out do those of the conventional esters to a degree.

8 Claims, 2 Drawing Figures

ORGANIC ESTER FOR USE IN LUBRICANT COMPOSITIONS

This is a continuation, of application Ser. No. 971,814 filed Dec. 21, 1978 now abandoned, which is a continuation of Ser. No. 908,357 filed May 22, 1978, now abandoned, which is a continuation of Ser. No. 731,992, filed Oct. 13, 1976, now abandoned.

This invention relates to organic products having an ester-like nature, to be employed in lubricating compositions, and more particularly it relates to esters which are obtained by reacting neopentyl-polyols and monocarboxylic acids, these compounds being such, due to their characteristics, as to be used with advantage, either alone or in the formation of lubricants for internal combustion engines.

Especially recommendable is their use in the formulation of multigrade oils, in that the advantages which can be achieved in such cases with the conventional esters, are still more conspicuous with the products contemplated by the present invention, on account of their quite special rheological properties.

Multigrade oils, in fact, in order to be able to fulfil the viscosity specification at 0° Fahrenheit and at 210° Fahrenheit are formulated by adopting appropriate fractions of mineral origin and suitable additives, as index-improvers.

It is often times necessary to resort to mineral fractions which are characterized by low viscosities (and thus they have a high volatility) in that their viscosity increase at low temperatures must be such as to maintain the viscosity of the entire formulation within the specified ranges.

It is just in such cases that the special esters as disclosed in the present invention prove to be most advantageous, inasmuch they, due to their being provided with viscosity indexes higher than those of the neopentylpolyolesters of the prior and contemporary art, allow less volatile mineral fractions to be employed and/or make it possible to reduce the percentage of the viscosity-index-improving additive. As an alternative, when the type and the percentages of the other components are kept constant, the esters in question permit considerably to improve the trend of the viscosity vs. temperature curve of the lubricant composition concerned.

The esters in question can be advantageously used, not only in admixtures which contain mineral oils, but also alone, by exploiting their paramount features, such as thermal stability, resistance to oxidation, lubricating power and a high viscosity index.

Broadly stated, the esters the subject of the present invention are the result of the reaction between the following:

(a) an admixture of a diol and a triol, in which the molar ratio of the diol to the triol lies within the range 1:2.5 to 1:10.

(b) an admixture of saturated monocarboxylic acids, as composed by two groups of I and II acids, to be defined as follows:

I—one or more saturated monocarboxylic acids containing from 8 to 10 carbon atoms;

II—one or more saturated monocarboxylic acids containing from 12 to 18 carbon atoms, said mixture being so characterized that the molar ratio of the acids of the I Group to those of the II Group lies within the range 2.5:1 to 18:1.

Preferably, the diol and the triol, are originated by alkenes which contain 5 or 6 carbon atoms. The diol is preferably of the pattern:

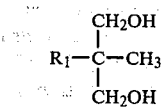

wherein $R_1$ is selected from among $-CH_3$ and $-C_2H_5$, and the triol is preferably of the pattern:

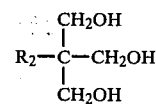

wherein $R_2$ is selected from among $-C_2H_5$ or $-CH_3$.

The monocarboxylic acids are of the type $R_3-COOH$, wherein $R_3$ is selected from among the alkyl radicals which contain either from 7 to 9 carbon atoms, or from 11 to 17 carbon atoms.

Examples of typical individuals are those in which the polyols are 2,2-di(hydroxymethyl)-propane (neopentylglycol, or NPG), and 1,1,1-tri-(hydroxymethyl)-propane (trimethylolpropane, or TMP), whereas examples of the acids are caprylic, pelargonic, capric acids for the I Group and lauric, myristic, palmitic and stearic acids for the II Group. Acids of natural origin, or straight-chained acids of synthetic origin can indifferently be used.

It is furthermore possible, on account of the expected properties, to introduce in the I Group branched-chain acids with $C_8$, $C_9$ or $C_{10}$, such as, for example, those acids which are obtained from oxosynthesis reactions. Also in the latter case, this invention affords considerable advantages over the conventional systems.

The reaction between the acids and the polyols concerned takes place as a single-step run and can be conducted in the presence, or not, of a solvent, such as for example benzene or toluene.

Esterification catalysts, such as benzenesulfonic acids, p-toluenesulfonic acids, methanesulfonic acids are preferably used whenever it is desired to increase the reaction velocity. The reaction, this notwithstanding, can equally well proceed without employing any catalysts.

The reaction temperatures can lie in the range from about 80° C. to about 260° C. and the reactions are preferably carried out in an inert gas atmosphere.

The various working procedures to follow in the reactions are those which, in general, are used and known in the esterification practice.

Figure 1:
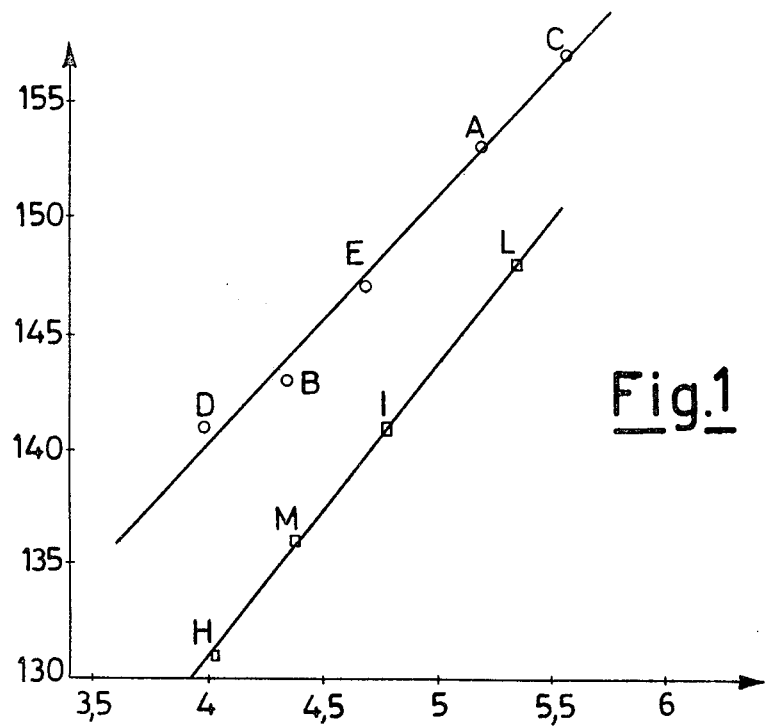
FIG. 1 is a plot of the relationship between 210° F. viscosity indexes of conventional products and a product of the invention.

The ensuing examples are illustrative of the present invention and the caracteristics of the products disclosed in the examples, as compared with those of the conventional products, are a showing of the achieved advantages.

EXAMPLE 1 (Product A)

0.415 mol of TMP-0.085 mol of NPG-1.019 mol of nonanoic acid-0.283 mol of dodecanoic acid-0.085 mol of palmitic acid-0.028 mol of stearic acid are reacted, with no solvent at all and in a nitrogen atmosphere. Methanesulfonic acid is employed as a catalyst.

After the reaction a stripping in nitrogen atmosphere is effected and the product is subsequently treated with aluminum oxide. The final acidity is 0.3 milligrams of KOH per gram. The viscosity, at 210° F. is 5.18 centistokes.

EXAMPLE 2 (Product B)

The reaction is conducted with 0.562 mol of TMP-0.187 mol of NPG-0.371 mol of dodecanoic acid-1.691 mol of a commercial "cut" of acids having an average mol.wt. of 154 (predominantly $C_8$ and $C_{10}$ acids).

The end product has an acidity of 0.2 milligrams KOH per gram and a viscosity at 210° F. of 4.34 centistokes.

EXAMPLE 3 (Product C)

The reactants are: 0.400 mol of TMP-0.050 mol of NPG-0.975 mol of nonanoic acid-0.195 mol of myristic acid-0.130 mol of palmitic acid.

The end product has a 210° F. viscosity of 5.56 centistokes.

EXAMPLE 4 (Product D)

The reactants are: 0.720 mol of TMP-0.280 mol of NPG-1.534 mol of octanoic acid-1.023 mol of nonanoic acid-0.163 mol of myristic acid. The product has a 210° F. viscosity of 3.99 centistokes.

EXAMPLE 5 (Product E)

The reactants are: 0.400 mol of TMP-0.100 mol of NPG-1.120 mol of a commercial "cut" of acids having an average mol. wt. of 154 (predominantly $C_8$ and $C_{10}$ acids)-0.140 mol of dodecanoic acid-0.140 mol of myristic acid. A product is obtained which has a 210° F. viscosity of 4.68 centistokes.

EXAMPLE 6 (Products F and G)

The reactants are: 0.500 mol of TMP-0.750 mol of octanoic acid-0.750 mol of isomeric $C_8$ acids. The product has a 210° F. viscosity of 4.54 centistokes and is the product F.

By reacting: 0.560 mol of TMP-0.140 mol of NPG-0.882 mol of octanoic acid-0.882 mol of isomeric $C_8$ acids-0.196 mol of myristic acid, a product is obtained, having a 210° F. viscosity of 4.56 centistokes, which is the product G.

Table 1 gives an overall view of the characteristics of the end products.

In the same Table, for comparison purpose, are reported the characteristics of the products which have been obtained with conventional procedures, that is to say, those of the esters which are formed by reacting TMP with octanoic acid (Product H), TMP with nonanoic acid (Product I), TMP with decanoic acid (Product L), TMP with a mixture of acids of from $C_7$ to $C_{12}$ (Product M).

TABLE 1

| Product | Viscosity at 0° F. centistokes | Viscosity at 100° F. centistokes | Viscosity at 210° F. centistokes | Viscosity index | Acidity milligm. KOH per gram |
|---|---|---|---|---|---|
| A | 598 | 25.21 | 5.18 | 153 | 0.32 |
| B | 417 | 19.72 | 4.34 | 143 | 0.20 |
| C | 670 | 27.60 | 5.56 | 157 | 0.20 |
| D | 346 | 17.46 | 3.99 | 141 | 0.20 |
| E | 488 | 21.90 | 4.68 | 147 | 0.20 |
| F | 801 | 24.00 | 4.54 | 118 | 0.05 |
| G | 648 | 22.92 | 4.56 | 125 | 0.25 |
| H | 414 | 18.38 | 4.03 | 131 | |
| I | 568 | 23.17 | 4.78 | 141 | |
| L | 700 | 26.93 | 5.34 | 148 | |
| M | 481 | 20.53 | 4.37 | 136 | |

The characteristics of the products H and I have been supplied by the technical literature, and those of the products L and M correspond to laboratory measurements on experimental products.

The viscosities of 0° F. which are too low to be factually measured with the Cold Crank Simulater, have been calculated, all of them, with the formula:

$$W_x = \frac{W_1 - W_2}{(\log T_2 - \log T_1)} (\log T_2 - \log T_x) + W_1$$

wherein $W_x$ is defined by the relationship: $W_x = \log \log (v_x + 0.6)$ in which $v_x$ is the viscosity in centistokes at the absolute temperature $T_x$. $W_1$ and $W_2$ are similarly defined.

The above reported formula, which makes it to obtain the viscosity $v_x$ at the temperature $T_x$ conveniently, once the viscosities $v_1$ and $v_2$ at the respective temperatures $T_1$ and $T_2$ are known, derives, like the ASTM charts, from the Walther equation, but permits a more accurate calculation while preventing the error inherent in the graphic proceedings.

The constant 0.6 is the one indicated by ASTM for viscosities higher than 1.5 centistokes.

Figure 2:
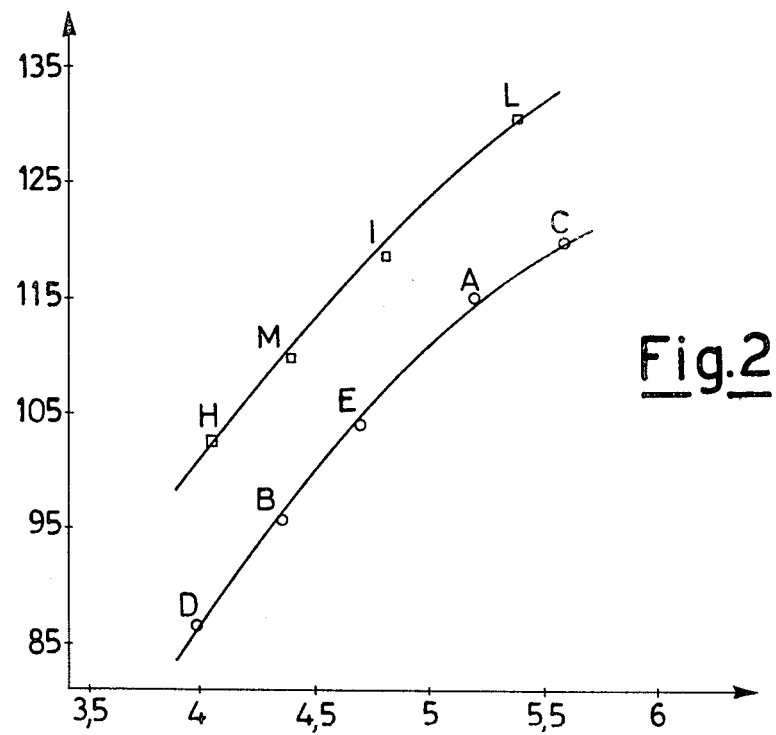
FIG. 2 is a plot of the relationship between 210° F. viscosity and the viscosity index of conventional products and a product of the invention.

In order that the differences between the conventional products and those obtained by the present Applicants may be made more conspicuous, the plots of FIGS. 1 and 2 have been prepared. Plot N° 1 indicates the relationship between the 210° F. viscosity and the viscosity indexes.

As is known, with the TMP series, the indexes are increased as the viscosity is increased. By examining now the lower curve relative to the conventional products, it can be appreciated that the trend of the characteristics, as it was predictable, is wholly regular irrespective of the kinds of the acids used, either alone or in admixture.

On examining now the upper curve, it can be seen that also the products according to the present invention show a surprising regularity of characteristics, as if they made up a class of esters of their own.

Their viscosity indexes, when the 210° F. viscosity is the same, are always higher than those of the conventional esters.

To have a more comprehensive comparison, there have been reported, in the plot N° 2, the ratios of the 0° F. viscosity to the 210° F. viscosity, as a function of the 210° F. viscosity.

Also in this case, the superior characteristics of the esters A, B, C, D, E are fully conspicuous, inasmuch as these esters have, when the 210° F. viscosity is the same, a lower 0° F. viscosity and, when the 0° F. viscosity is the same, have a higher 210° F. viscosity. Furthermore, Example 6 shows that, even when branched-chain acids are present, the method as followed by the present Applicants makes it to obtain products which possess improved characteristics.

As a matter of fact the products F and G, which both contain straight-chain $C_8$ acids and branched-chain $C_8$ acids in the ratio of 1:1, have the respective viscosity indexes of 113 and 125, even though they have the same viscosity at 210° F.

The advantages inherent in the synthetic bases as disclosed in the present application are likewise detected in the lubricants which contain them. To give an evidence of this fact, TABLE 2 reports the characteristics of three multigrade oils: the oil P has been prepared with the ester B, a mineral oil having a high viscosity index, a commercial polymer V.I.I. (Viscosity Index Improver) and a package of commercial additives.

The oil Q contains the same package of additives and the same type of V.I.I. polymer, but does not contain synthetic bases. Consequently, to improve its rheological characteristics, a high percentage of a high-index fluid mineral oil has been introduced in the formulation. This notwithstanding, the viscosity at 0° F. rose from 2900 centipoises to 3700 centipoises, even though the 210° F. viscosity had dropped a little.

By making a similar comparison between the oil Q and the oil S which is distinguished over the oil P for containing the conventional ester M, it can be seen that the 0° F. viscosities differ by 500 centipoises, whereas between the P and Q oils, such difference was 800 centipoises.

TABLE 2

|  | Oil P | Oil O | Oil S |
| --- | --- | --- | --- |
| Solvent Neutral 125, % | — | 47,7 | — |
| Solvent Neutral 500, % | 44 | 36,0 | 44 |
| V. I. I. polymer, % | 8 | 8,3 | 8 |
| Ester B, % | 40 | — | — |
| Ester M, % | — | — | 40 |
| Package of additives, % | 8 | 8 | 8 |
| Viscosity at 210° F. centistokes | 18,24 | 17,90 | 18,30 |
| Viscosity at 0° F. (CCS) centipoises | 2900 | 3700 | 3200 |

What we claim is:

1. A mixture of esters, for use in a lubricating composition, said esters being prepared by a process which consists of the esterification of:
(a) a mixture of bifunctional and trifunctional pentylpolyols wherein the molar ratio of the bifunctional neopentylpolyols to the trifunctional neopentylpolyols as in the range of 1:2.5 to 1:10 and
(b) a mixture of saturated monocarboxylic acids consisting of:
Group I, containing one or more acids having from 8 to 10 carbon atoms; and
Group II, containing one or more acids having from 12 to 18 carbon atoms; the molar ratio of the acids in Group I to the acids in Group II being in the range from 2.5:1 to 18:1.

2. A mixture of esters as claimed in claim 1 in which the bifunctional neopentylpolyol has the formula:

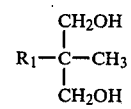

wherein $R_1$ is —$CH_3$ or —$C_2H_5$, and the trifunctional neopentylpolyol has the formula:

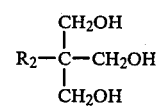

wherein $R_2$ is —$C_2H_5$ or —$CH_3$.

3. A mixture of esters as claimed in claim 1, wherein the saturated monocarboxylic acids of Group I are straight-chained acids represented by the formula $R_3$-COOH wherein $R_3$ is an alkyl radical which contains from 7 to 9 carbon atoms and the saturated monocarboxylic acids of Group II are straight-chained acids represented by the formula $R_4$-COOH wherein $R_4$ is an alkyl radical which contains from 11 to 17 carbon atoms.

4. A mixture of esters as claimed in claim 1 wherein Group I contains at least one branched-chain acid.

5. A mixture of esters as claimed in claim 1, wherein the bifunctional neopentylpolyol is 2,2-di-(hydroxymethyl)-propane, and the trifunctional neopentylpolyol is 1,1,1-tri(hydroxymethyl)-propane.

6. A lubricating composition containing the product of claim 1 as a major constituent.

7. A mixture of esters as in claimed in claim 1 wherein the acid of Group I is an acid having 9 carbon atoms.

8. A mixture of esters as claimed in claim 1 wherein the acid of Group I is an acid having 10 carbon atoms.

* * * * *